United States Patent [19]

Janocik et al.

[11] Patent Number: 5,193,678
[45] Date of Patent: Mar. 16, 1993

[54] APPARATUS FOR COUNTING AND DISPOSING OF EXPENDABLE MEDICAL ITEMS, INCLUDING SHARPS AND THE LIKE

[75] Inventors: Michael T. Janocik; Larry D. Potts, both of Louisville, Ky.

[73] Assignee: Packaging Service Corporation of Kentucky, Louisville, Ky.

[21] Appl. No.: 849,938

[22] Filed: Mar. 12, 1992

[51] Int. Cl.⁵ ..................... B65D 83/02; B65D 83/10
[52] U.S. Cl. ............................. 206/363; 206/366; 206/368; 206/370; 206/818
[58] Field of Search ............... 206/363, 366, 369, 370, 206/818

[56] References Cited

U.S. PATENT DOCUMENTS

| | | | |
|---|---|---|---|
| 4,418,821 | 12/1983 | Sandel | 206/370 |
| 4,714,168 | 12/1987 | Johnson et al. | 206/366 X |
| 4,715,498 | 12/1987 | Hanifl | 206/366 |
| 4,736,844 | 4/1988 | Scott et al. | 206/370 |
| 4,828,107 | 5/1989 | Spencer | 206/366 |
| 4,842,138 | 6/1989 | Sandel et al. | 206/366 |
| 4,890,733 | 1/1990 | Anderson | 206/366 |
| 4,903,390 | 2/1990 | Vidal et al. | 30/151 |
| 4,922,597 | 5/1990 | Ikeda et al. | 206/366 |
| 5,046,614 | 9/1941 | Torres et al. | 206/366 |
| 5,076,429 | 12/1991 | Patrick et al. | 206/370 |
| 5,107,990 | 4/1992 | Wicherski et al. | 206/366 |

Primary Examiner—William I. Price
Attorney, Agent, or Firm—Middleton & Reutlinger

[57] ABSTRACT

In operation of the apparatus of the preferred embodiment, a used surgical sharp is placed into a drop window or receiving opening. Once the sharp is resting upon the partial floor of the housing assembly, the user will engage a safety slide having a pinch style cutter mechanism, so that a mandrel and blade converge and shear any remaining suture material from a needle. This also closes a window protector over the receiving opening. A magnet properly aligns metal items for disposal. Once any suture material is cut from the needle, a safety device consisting of opposing intermeshable rakes sweeps the sharp along the partial floor and into the drop window. This sweeping motion is created by the user moving the shuttle assembly from front to rear from a first to a second position. The shuttle assembly must be moved to the second position before it can be returned to the first position. A counter is then engaged to advance one increment. The safety rake system assures that the counter is advanced if and only if a sharp is introduced and cycled through the apparatus. If no sharp is between the two rakes to present an obstruction between the rakes, the tines of the rakes will intermesh and the counter will not be advanced. The sharp falls through the drop window and into the drop area of a disposable receptacle. Combs ensure the sharp doesn't "stick" to the rake tines. The sharp count is accumulated numerically by the mechanical counter.

23 Claims, 6 Drawing Sheets

APPARATUS FOR COUNTING AND DISPOSING OF EXPENDABLE MEDICAL ITEMS, INCLUDING SHARPS AND THE LIKE

BACKGROUND OF THE INVENTION (a) Field of the Invention

The present invention relates to containers for the accounting and disposing of expendable medical items, including operating room sharps, such as, for example, suture needles and scalpel blades.

Accounting for operating room sharps is a safety measure, designed to decrease the risk of patient injury. Without an accurate sharps accounting system, the risk of inadvertently leaving and overlooking a suture needle or scalpel blade in a patient's body is believed to be significantly increased. The number of used sharps accounted for at the completion of the procedure should equal the number of sharps introduced during the procedure. By disposing of each sharp individually in an apparatus which accurately counts the sharps and places them in a secure receptacle, if the count on the disposal apparatus at the completion of a procedure matches the sharps used, then one can conclude with a high degree of confidence that all sharps have been accounted for and the risk of patient injury due to a misplaced sharp is minimized.

The safe disposal of used operating room sharps is also important. Since sharps are normally used to penetrate or cut human tissue, there is a possibility that used sharps have been contaminated with infectious material. Throughout the disposal process, the user should be sufficiently protected against sharp or needle sticks.

(b) Description or Prior Art

The current method of counting and disposing of used operating room sharps relies on a small open plastic "box" or container that incorporates a visual aid, usually sequential numbers printed in a matrix on the base of the box. The base is often contains a block of flexible foam material or a magnetic sheet. The foam block and/or magnetic sheet serve as a means to secure the used sharps in the plastic container. During surgical procedures, once a sharp is used, it is sequentially secured in the plastic container in a numbered slot. To secure the sharp, the sharp is forced into the foam block or strip, or laid on the magnetic sheet. Any remaining suture material is cut from the needle either before or after the sharp is secured in the box. At the end of the surgical procedure, the sequentially secured used sharps are counted and the results are verified against a predetermined count. If the actual ending count matches the predetermined count, then, the likelihood of a sharp being inadvertently left in the patient's body is minimized.

There are significant problems associated with the current counting system. First, the difficulty in securing the sharp into a numbered slot within the confines of a small container presents handling problems for the user. These handling problems introduce a potential safety hazard because the sharps may be contaminated. Further, they reduce operating room efficiency. Second, the accuracy of the count is prone to human errors. Often, by the end of the procedure, there can be as many as 120 different sized sharps contained in one small needle counter. This high concentration of sharps makes it very difficult to visually ensure an accurate count. Third, due to the variance in the number and type of surgical procedures being performed in any given institution, the purchasing and storing of different styles of needle counters results in potential inventory problems. Fourth, since the current needle counters encompass a variety of materials and processes, environmental disposal issues are raised.

The known prior art teaches disposal systems having rotatable trays, hinged lids, pivoting chutes, and the like. No prior art is known teaching a sharps disposal apparatus having a drop window with a safety shutter, an automatic counter, or a pinch cutter.

U.S. Pat. No. 5,076,429 teaches a sharps container 10 having a bucket 12, lid 14, and tray 16. Tray 16 receives sharps and is rotated by flats or handle 22 to place them into bucket 12. Baffle flap 40 seals the container.

U.S. Pat. No. 5,046,614 teaches a needle and sharps disposal container 10 having a hollow container body 12 and top 14. Top 14 has partial stationary cylinder 22 with surfaces 18 and 20 and slot 34 to receive needles and sharps for disposal; rotatable cylinder 22 being contained in stationary cylinder 24.

U.S. Pat. No. 4,903,390 teaches a scalpel blade removal apparatus 40 for removing blades 14 from scalpel handle 12 and retaining blades 14 in housing 42.

U.S. Pat. No. 4,890,733 teaches a disposal receptacle for used sharps, etc. Receptacle 10 comprises a bucket 14 with cover 18. Cover 18 has chute 32. Pivotally mounted scoop 50 receives items to be disposed.

U.S. Pat. No. 4,842,138 teaches a container 10 comprising a bottom part 20, a top part 30, a sliding cover 60, and a pair of cover rails 70A and 70B. Rectangular barrier flap 50 swings inwardly into container 10 when items are inserted. In addition to large opening 44, smaller opening 46 is included for receiving smaller, more specific items, such as "Luer" and "Vacutainer"-type hypodermic needles.

U.S. Pat. No. 4,828,107 teaches a disposable container 10 for syringes: container 10 having body 12, cover 14, and dome 16. Lever 20 and dump tray 18 are used to place items into body 12.

U.S. Pat. No. 4,736,844 teaches a sharps disposal container 1 with compartments 2 and 3. Lid 4 closes compartment 3. Compartment 2 has slot 13 to receive scalpel blades 21. Needles from sutures 22 and hypodermic syringes 23 are inserted into dense foam strips of compartment 3. Smaller items are stuck to adhesive layer 9. Items can be manually counted and container 1 then incinerated.

U.S. Pat. No. 4,715,498 teaches a sharps disposal system 10 having outer enclosure 12 and inner container 14. Outer enclosure 12 has opening 34 defined by shelf 32 and cowl 28. Tab 70 is moved to open closure 48 to receive items for disposal.

U.S. Pat. No. 4,714,168 teaches a container having a lower body 2 and upper body 4. Handle 30, wall 24, and lid 16 are pivoted together so that items to be disposed can be inserted.

U.S. Pat. No. 4,418,821 teaches using foam blocks 11 with numbers 12 to manually receive needles 14 and magnetic strip 13 to receive surgical blades 15.

DEFINITIONS

Throughout the application, the following terms are used as defined below.

(a) Alignment Magnet—Bar magnet contained in the partial floor of the housing assembly which aligns a metallic item to be disposed such that the item's major axis will be perpendicular to rake teeth, or tines.

(b) Comb—Shuttle assembly component which sweep or "comb" off any item being disposed which might hang onto the rakes during the return stroke of the shuttle assembly from the second position to the first position.

(c) Counter—Mechanical counting device contained in the housing assembly which numerically counts each item to be disposed that is "shuttled" through the device.

(d) Counting Actuator—"V"-shaped device contained in an actuator recess in the housing assembly partial floor which is engaged when an item to be disposed is present and engages the counter advancer means.

(e) Force—Component of the shuttle assembly which links the user input motion to the rakes and combs when slidably moving the shuttle assembly.

(f) Front Rake—Component of the shuttle assembly which pushes items to be disposed along the housing assembly partial floor to be deposited into the removable receptacle when the shuttle assembly is moved from the first to second position.

(g) Housing Assembly—Assembly containing the counter and the removable receptacle and retaining the slidably movable shuttle assembly.

(h) Needlecount—a device used to facilitate the accounting of and disposal of operating room sharps.

(i) Rear Rake—Component having a rib which engages the counting actuator if an item to be disposed is present, but which does not engage the counting actuator if no item to be disposed is present because the rear rake and front rake tines intermesh.

(j) Retainer—Housing assembly component which secures or "retains" the slidable shuttle assembly.

(k) Scalpel—a small thin bladed knife used especially in surgery.

(l) Scalpel Blade—a small thin blade used with scalpel knife.

(m) Sharp—a sharp instrument used during surgical procedures for the purposes of cutting or sewing tissue, such as, for example, suture needles and scalpel blades.

(n) Shuttle Assembly—Top portion of reusable needlecount device, which "shuttles" back and forth from a first to second position with application of force by a user.

(o) Shuttle Position Means—Spring assembly contained in a "C"-shaped recess in the housing assembly partial floor which ensures that the shuttle assembly must be moved all the way to the second position from the first position before the shuttle assembly can be returned to the first position.

(p) Suture—a length of strand or filament material used to sew or stitch human tissue.

(q) Suture Needle—a straight or curved needle terminated at a butt end with a length of suture used for sewing and stitching human tissue.

SUMMARY OF THE INVENTION

The present invention is for an apparatus for counting and disposing of expendable medical items, including sharps and the like. The object of this system is to provide a safe and effective way to count and dispose of items, such as used operating room sharps.

There is provided a housing assembly having a counter and a removable receptacle. The housing assembly has a partial floor therein. A shuttle assembly is slidably received in and retained by the housing assembly. The shuttle assembly has a receiving opening to receive items to be disposed. When an item is placed in the receiving opening, it falls to the housing assembly partial floor. The shuttle assembly is slidably moved from a first to second position and the item to be disposed is moved along the partial floor to fall into the removable receptacle. The counter is advanced to the next number.

According to other embodiments of the present invention, there are provided a reusable shuttle assembly having a mandrell and cutting blade which shears any remaining suture material from an item to be disposed; a safety slide having a window protector which protects the user disposing of an item; a rake and comb assembly, controlled by a force, which moves the item to be disposed to the removable disposable container included in the housing assembly; and, an actuator which advances the counter only if an item is present. The counter is resettable when a container is inserted into the housing assembly. The counter can be viewed from a window in the shuttle assembly.

More particularly, the present invention comprises an apparatus for counting and disposing of expendable medical items, including sharps and the like, comprising: a housing assembly, the housing assembly including a counter and a removable receptacle for depositing items for disposal, the housing assembly having a partial floor therein; the housing assembly having a front and a rear; the counter having engagement means to advance counter to the next number; and, a movable shuttle assembly slidably received in and retained by the housing assembly, the shuttle assembly having a receiving opening therein, such that any item received into the receiving opening will be received on the partial floor of the housing assembly, whereby, when the shuttle assembly is slidably moved from a first position to a second position, any item on the partial floor is deposited in said removable receptacle and the counter advancer means is engaged to advance the counter to the next number.

Finally, in addition, the present invention may also include a window in the shuttle assembly for viewing the counter; means to reset the counter when the removable receptacle is included into the housing assembly; means to position the movable shuttle assembly at the first position and necessitate that when the shuttle assembly is slidably moved, the movable shuttle assembly must be moved to the second position before the movable shuttle assembly can be returned to the first position; means to only engage the counter advancer means when the shuttle assembly is moved from the first position to the second position and an item has been deposited into the receiving opening and received on the partial floor of the housing assembly; means to comb items from the front rake tines and the rear rake tines; means to properly align the items for disposal received on said partial floor of the housing assembly; means to close the receiving opening in the shuttle assembly; and, means to cut.

BRIEF DESCRIPTION OF THE DRAWINGS

A better understanding of the present invention will be had upon reference to the following description in conjunction with the accompanying drawings, wherein.

DETAILED DESCRIPTION OF THE PREFERRED EMBODIMENT

Figure 1:
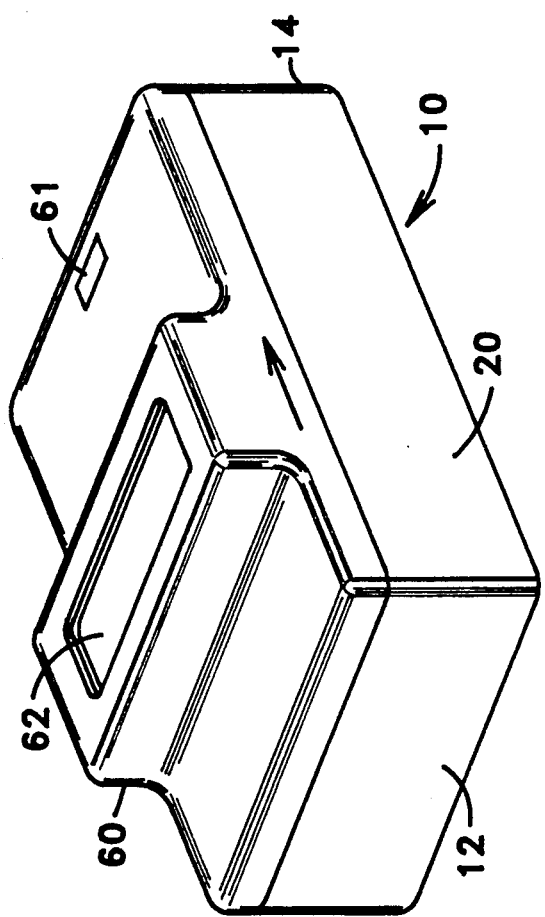
FIG. 1 is a perspective view of one preferred embodiment of the sharps counting and disposal system of the present invention showing the shuttle assembly at its first position.
Figure 2:
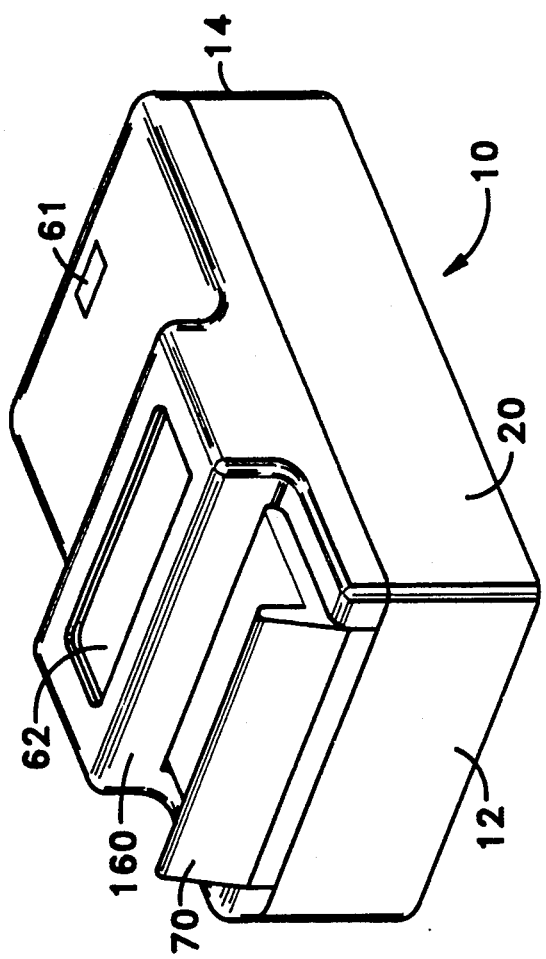
FIG. 2 is a perspective view of another preferred embodiment of a sharps count and disposal system of the present invention having a safety slide and blade cutter incorporated therein.

FIGS. 1 and 2 show two preferred embodiments of the counting and disposal apparatus 10 of the present invention. With reference to FIG. 1, apparatus 10 is shown having a reusable housing assembly 20 having a disposable receptacle 90, shown later, inserted therein. Housing assembly 20 has a front 12 and a rear 14. Movable shuttle assembly includes shuttle 60, shown in a first position. As will be explained later, shuttle 60 can be moved in the direction of the arrow shown to a second position. Because of the dimensions of the items to be disposed, we believe that it is preferable that the distance from the first to second position be at least one and three-eights inches (1⅜"). Receiving opening 62 is for the depositing of expendable items to be disposed. A counter, shown later, can be viewed through window 61.

With reference to FIG. 2, the shuttle assembly is shown including shuttle 160 having safety slide 70. These comprise the means to close receiving opening 62 and the means to cut any material attached to any item to be disposed, for example, suture filament remaining attached to a suture needle, before slidably moving the shuttle assembly from the first to second position. Preferably, for safety, it is envisioned that a first amount of force will be required to move the safety slide 70 toward the rear 14 of housing assembly 20 thereby closing receiving opening 62 and cutting any attached material and an additional amount of force, exceeding the first amount of force, will be required to then move the shuttle assembly from the first to second position.

Figure 3:
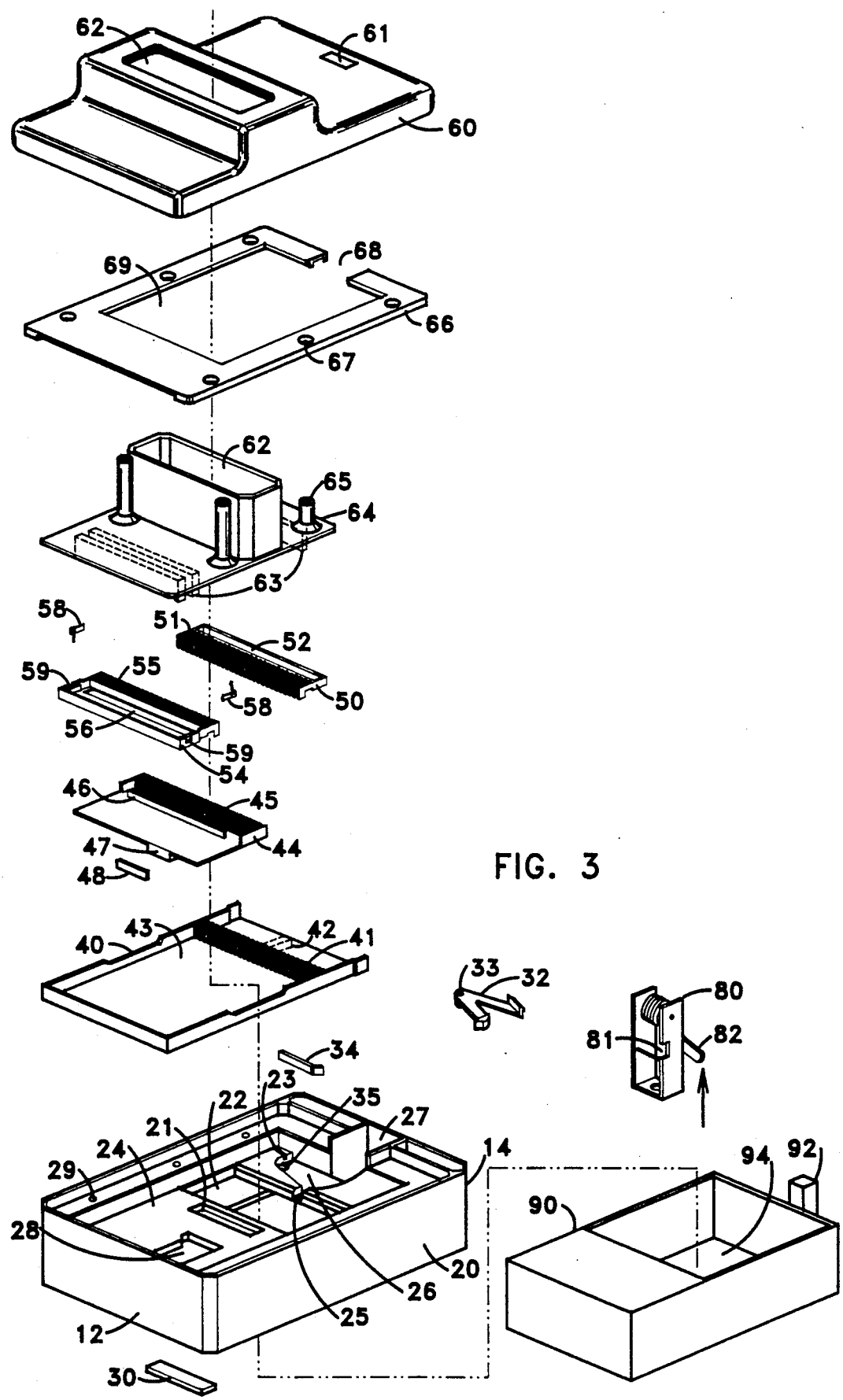
FIG. 3 is an exploded view of the system of FIG. 1, showing the major components.

FIG. 3 shows an exploded view of the major components of the apparatus of FIG. 1. Housing assembly 20 can be fabricated from any suitable material, such as, for example, high temperature injection moldable plastic resin material or machineable metal material. Housing assembly 20 has a partial floor 24 therein. Partial floor 24 contains drop window 22 therethrough. When the shuttle assembly is at the first position, as discussed with FIG. 1, the area of the partial floor 24 beneath receiving opening 62 is the resting place for items to be disposed which are dropped through the shuttle 60 receiving opening 62. The item then rests on the partial floor 24 until the user slidably moves the shuttle assembly from the first to the second position. The item is then "raked" along partial floor 24 to the drop window 22. This operation will be fully explained later.

Partial floor 24 of housing assembly 20 also contains numerous recesses or receptacles which receive other components described hereinafter. Magnet receptacle 21 preferably lies beneath receiving opening 62 and contains a bipolar magnet 30, whose poles function to physically align metal items to be disposed, such as, for example, sharps and needles, so that they are in a parallel alignment with front 12 or rear 14 and thereby preventing an obstruction when slidably moving the shuttle assembly from the first to second position. Magnet receptacle 21 can either be in the top or bottom of partial floor 24, as magnet 30 is preferably sealed therein, being close to the top surface of partial floor 24. Magnet receptacle 21 and magnet 30 are an example of a means to properly align items for disposal received on partial floor 24.

Partial floor 24 has other recesses in its top surface: actuator-engaging rib recess 25; actuator recess 26 having an upwardly extending actuator mount 35; actuator spring recess 23; counter recess 27; "C"-shaped recess 28; and six screw boss recesses 29. These will be explained in more detail later when discussing the components the recesses receive.

Counter 80 is preferably a sequential numerical mechanical counter. Counter 80 has a counter advancer means 81. Counter 80 also has a reset tab 82 which, when engaged, initializes the counter 80 to a "zero" reading, and the operation of which will be explained in conjunction with receptacle 90. Counter 80 is contained in counter recess 27. The mechanical counter 80 we are currently employing is fabricated from aluminum tumblers with stainless steel drive components. The tumblers of the counter are finished in black through an anodizing process. The numbers on the tumblers are natural or polished aluminum to lend contrast to the black background.

Removable receptacle 90 is ideally disposable and made from any suitable material, such as, for example, a low grade injection moldable plastic or rigid paper. The receptacle 90 has a drop area 94 and a counter resetter 92. Receptacle 90 is included into housing assembly 20 from underneath partial floor 24. Drop window 22 in partial floor 24 is atop drop area 94. Counter resetter 92 and reset tab 82 comprise a means to reset counter 80 when receptacle 90 is included into housing assembly 20. When a new receptacle 90 is included into housing assembly 20, resetter 92 engages reset tab 82, causing counter 80 to reset to "zero". Removing receptacle 90 for disposal does not reset counter 80. Therefore, the last counter 80 reading is retained on the counter face until a new receptacle 90 is included.

Shuttle 60 can be fabricated from any suitable material, such as, for example, injection moldable high temperature plastic resin or from metal. Shuttle 60 has a receiving opening 62 large enough to accept the items to be disposed, including any size surgical needle currently available. Toward the rear 14, shuttle 60 has a clear window 61 that allows the user to view the mechanical counter tumblers.

As the shuttle assembly is slidably received in and retained by housing assembly 20, the raised portion of the shuttle 60 has four holes (not shown) to accept fasteners and thereby retain the shuttle assembly in housing assembly 20. The shuttle 60 functions to provide a smooth user interface, as well as to cover the interior components of the apparatus 10.

Force 64 can be fabricated from any suitable material, such as, for example, high temperature injection moldable plastic resin material or machineable metal material. Force 64 also contains receiving opening 62. Force 64 has four screw bosses 65 to be used to attach force 64 to the four holes in the raised portion of shuttle 60. Force 64 is shown with three parallel force rails 63 on its bottom surface. Rails 63 are downwardly-extending and rectangular-shaped. The front two rails 63 are positioned to the front 12 side of receiving opening 62. The third rear rail 63 is to the rear 14 side of receiving opening 62. The function of rails 63 will be explained later.

Rear rake 40, front rake 44, rear comb 50, and front comb 54 can be made from any suitable material, such as, for example, high temperature injection moldable plastic resin or machineable metal material.

Rear rake 40 is rectangular-shaped and has opening 43 therethrough. Opening 43 is in alignment with receiving opening 62. Opening 43 is created by a pair of parallel side rails, a front rail connecting the parallel side rails toward the front 12 of housing assembly 20, and a counter actuating assembly connecting the parallel side rails toward rear 14 of housing assembly 20. The counter actuating assembly has a plurality of rear rake tines 41 opening toward the front 12 of housing assembly 20 and a surface behind the plurality of tines toward the rear 14 of housing assembly 20. The surface has a downwardly-extending actuator-engaging rib 42 which is parallel to the parallel side rails and approximately half way between them. In the embodiment shown, the rear rake 40 has twenty-four tines 41. Rear rake 40 rides on partial floor 24 such that the actuator-engaging rib 42 can slide in actuator-engaging rib recess 25.

Rear comb 50, as shown, has twenty-five rear comb tines 51 that intermesh with and are slidable between the rear rake tines 41. As will be explained later, rear comb 50 functions to comb off any item that might cling to rear rake 40. Tines 51 open toward the front 12 of housing assembly 20. Rear comb force rail receptacle 52 is located toward rear 14 of housing assembly 20 as related to tines 51. Rear comb 50 rides on top of the surface of rear rake 40. Receptacle 52 receives single rear force rail 63, and the sized relationship between receptacle 52 and rail 63 determines the relative movement allowed between tines 41 and tines 51. The tines 51 of the rear comb 50 have a concave face. This concavity functions to "lift" the item to be disposed from the partial floor 24 so that the item will not become jammed between the tines 41 and 51 and the partial floor 24.

Front rake 44, as shown, has twenty-five front rake tines 45 which can intermesh with the twenty-four rear rake tines 41 if there is no item to be disposed, as will be explained later. Tines 41 open toward the rear 14 of housing assembly 20. The faces of the tines 41 are concave in shape to "lift" an item to be disposed as it is pushed along the partial floor 24 when moving the shuttle assembly from the first position to the second position. This lifting motion prevents the item from becoming jammed between the tines 45 and the partial floor 24 during disposal.

The front rake 44 has a surface before the tines 41 toward the front 12 of housing assembly 20. This surface has an upwardly-extending, rectangular-shaped, protruding rail 46, which is parallel to and received by the two front force rails 63. This surface has a downwardly-extending support 47 having a slot therein. The slot contains a rectangular-shaped flat spring 48. Front rake 44 rides on partial floor 24 with support 47 and spring 48 received by C-shaped recess 28, thereby providing a means which necessitates that when the shuttle assembly is to be moved from the first position, it must be moved all the way to the second position before it can be returned to the first position. The same applies when moving the shuttle assembly from the second to first position. The C-shaped recess 28 has a C-side. The recess 28 opening width on the C-side is wider at both the front 12 and rear 14 position portions than therein-between. The width from the front and rear position portions taper down to the width of the thereinbetween portion to ease movement of spring 48. The front and rear positions are sized to allow spring 48 to relax when contained therein. In operation, when the movable shuttle assembly is at its first position, the rectangular-shaped spring 48 is in a relaxed condition in the front position of the C-shaped recess 28; when the movable shuttle assembly is slidably moved toward the second position, the rectangular-shaped spring 48 bends toward the front 12 position by engaging the C-side, thereby preventing the movable shuttle assembly from being returned to the first position until the movable shuttle assembly is at the second position, where the rectangular-shaped spring 48 is again in a relaxed condition in the rear 14 position of said C-shaped recess 28. Spring 48 functions in the same way when returning the shuttle assembly from the second to the first position.

Front comb 54, as shown, has twenty-four front comb tines 55 that intermesh with and are slidable between front rake tines 45. As will be explained later, front comb 54 functions to comb off any item that might cling to front rake 44. Tines 55 open toward the rear 14 of housing assembly 20. Front comb force rail receptacle 56 is located toward front 12 of housing assembly 20 as related to tines 55. Front comb 54 rides on top of the surface of front rake 44. Receptacle 56 receives protruding rail 46 and the pair of front force rails 63, and the sized relationship between receptacle 56 and rails 46 and 63 determines the relative movement allowed between tines 45 and tines 55.

As shown, front comb 54 has a pair of comb spring notches 59 which receive comb springs 58. Comb springs 58 creates a pressure, and thereby a frictional force, between the parallel side rails of the rear rake 40 and front comb 54. The tines 55 of the front comb 54 are shaped in a concave fashion to "pick up" the item being disposed, so that the item does not become lodged between the tines 55 and the partial floor 24.

The number of tines 41, 45, 51, and 55 can be easily modified for other embodiments, as desired by the maker. However, the spaced and number relationships between the tines 41, 45, 51, and 55 should be maintained so that the intermeshing of the front rake tines 41 and rear rake tines 51, the sliding of front comb tines 55 within front rake tines 45, and the sliding of rear comb tines 51 within rear rake tines 41 is not interfered with. These tine interactions will be explained later with the discussion of FIG. 6.

"V"-shaped actuator 32 has a front tip, a rear tip, a base end, and a downwardly-extending bore 33 therethrough at the base end. Actuator 32 can be manufactured of any suitable material, such as, for example, high temperature injection molded plastic resin or machineable metals. Actuator 32 is mounted onto actuator mount 35, contained in actuator recess 26 in the partial floor 24 of housing assembly 20, by placing actuator bore 33 onto mount 35. Actuator spring recess 23 contains actuator spring 34, such that, in a rest position, actuator spring 34 positions actuator 32 so that the rear tip of the actuator does not engage the counter advancer means 81 when the shuttle assembly is at the first position.

As will be explained further with FIG. 6, if an item to be disposed is received on partial floor 24 and the shuttle assembly is moved from the first to second position to dispose of the item, the actuator-engaging rib 42 will slide toward rear 14 in actuator-engaging rib recess 25 in partial floor 24 of housing assembly 20 to engage the front tip of actuator 32. Actuator 32 then rotates about mount 35 toward rear 14 causing the rear tip of actuator 32 to engage counter advancer means 81 and advance the reading on counter 80 to the next highest number. Actuator 32 is "V"-shaped with its front tip having a unique "head". The "head" has an approximately 45 degree sloping face extending toward front 12. When this sloping face engages rib 42, the location at which the sloping face and rib 42 engage slides across the rear 14 end of rib 42 as rear rake 40 is moved toward rear 14. This results in less displacement toward rear 14 of actuator 32's rear tip than of rib 42. Actuator 32's rear tip is shaped to properly engage counter advancer means 81.

Retainer 66 is shown having opening 69 therethrough. Opening 69 allows force 64 to pass therethrough so that screw bosses 65 can be attached to shuttle 60, but also is sized so that housing assembly 20 can slidably retain force 64, and thereby the shuttle assembly. This is accomplished by bores 67 being aligned on the screw bosses 29 of housing assembly 20 and attaching retainer 66 to housing assembly 20 using, for example, screws. Retainer 66 also has a counter notch 68 so that counter 80 is visible through window 61 when the shuttle assembly is at its first position. Retainer 66 can be fabricated from any suitable material, such as, for example, high temperature injection moldable plastic resin material or other high temperature materials. As is seen, retainer 66 functions to secure the interior components of the shuttle assembly of apparatus 10, namely the rakes 40 and 44, combs 50 and 54, and force 64.

Figure 4:
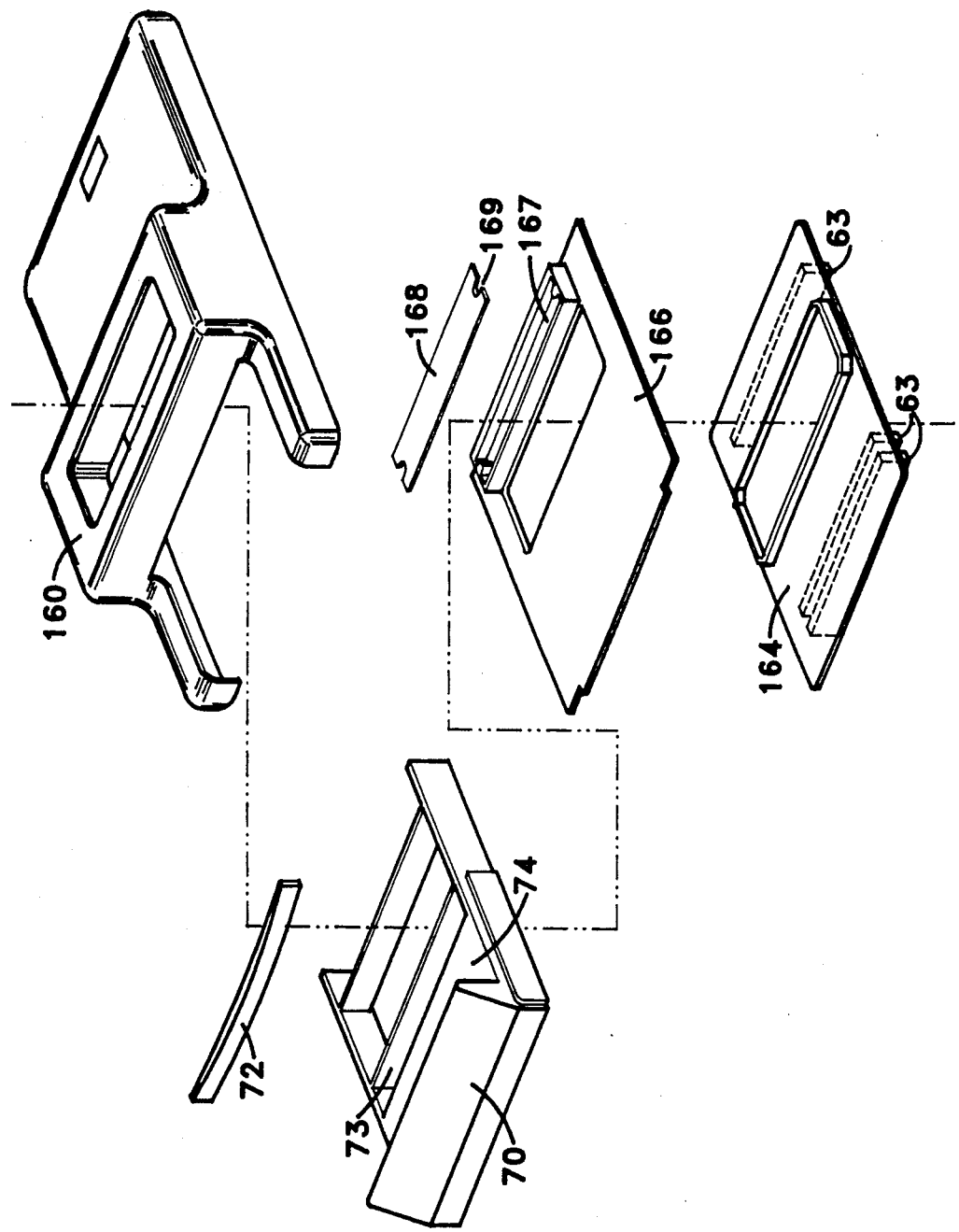
FIG. 4 is an exploded view of the safety slide and blade cutter mechanisms of FIG. 2.
Figure 5:
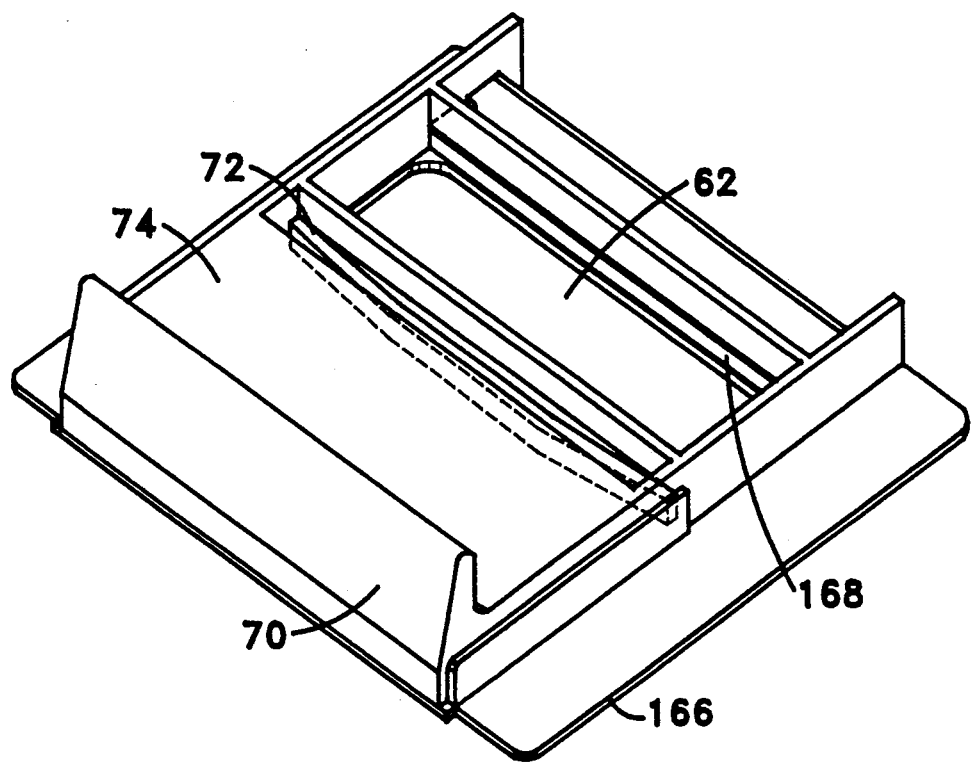
FIG. 5 is a partway assembled system of FIG. 2, showing the relationship between the safety slide, the mandrell, and the blade; and, FIGS. 6A–6F demonstrate the comb and rake actions when "shuttling" to dispose of an item.

Before explaining the rake and comb actions, an additional embodiment of the shuttle assembly is shown in FIGS. 4 and 5. These figures show the addition of means to close receiving opening 62 in the shuttle assembly for safety and means to cut any material attached to an item to be disposed but extending from receiving opening 62. Safety slide 70 is shown as being receivable into a safety slide opening in modified shuttle 160 toward front 12. Safety slide 70 has a window protector 74 toward front 12 of housing assembly 20 and an opening therebehind. Safety slide 70 has an open position, wherein the opening is aligned with receiving opening 62 and partial floor 24 therebelow, such that items to be disposed can be received by receiving opening 62 and received onto partial floor 24 therebelow. Safety slide 70 also has a closed position, wherein the safety slide 70, and thereby window protector 74, is moved toward rear 14, and window protector 74 comes between receiving opening 62 and the partial floor 24 therebelow, thereby protecting a user when sliding the shuttle assembly from the first to the second position.

Plate 166 is also shown. Plate 166 has an opening therethrough, the opening being in alignment with receiving opening 62 and partial floor 24 therebelow. The opening has a front side and a rear side. The plate 166 has a raised blade receptacle 167 located toward rear 14, in relation to the opening in the plate 166. A cutting blade 168 is shown having notches 169 which permit blade 168 to be securely mounted in the blade receptacle 167. Blade 168 is in a parallel alignment with plate 166 and extends into the opening in plate 166 from the rear side toward the front side.

Also shown is a curved, rectangular-shaped, mandrell 72. Mandrell 72 is inserted into mandrell slot 73 in safety slide 70. Mandrell 72 is located between window protector 74 and the opening therebehind. Mandrell 72 is perpendicular to cutting blade 168. When safety slide 70 is slidably moved from its open position to its closed position, mandrell 72 engages cutting blade 168 to shear from any item received into the receiving opening 62 any portion of the item extending thereabove opening 62. Force 164 has been modified from force 64, as required for this embodiment, but force 164 functions as did force 64, and will again be retained by retainer 66, as previously shown. It is envisioned that the components of FIGS. 4 and 5 will be appropriately attached by, for example, ultrasonic welding, rather than screwing.

Now with reference to FIGS. 6A–6F, the spaced relationships of rakes 40 and 44 and combs 50 and 54, relative to each other and relative to actuator 32, are shown in example. Curved sharp 101 is being disposed and the shuttle assembly is being moved from the first position to the second position and back to the first position.

Rakes 40 and 44 provide a means to only engage counter 80 advancer means 81 when the shuttle assembly is moved from the first position to the second position and an item to be disposed has been deposited into receiving opening 62 and received on partial floor 24 therebelow. Combs 50 and 54 provide a means to comb items to be disposed from front rake tines 45 and rear rake tines 41.

FIGS. 6A–6F show sharp 101 being disposed. However, if sharp 101 was not there, it is seen that when the shuttle assembly is moved from the first to the second position, the front rake tines 45 will intermesh with the rear rake tines 41 and actuator-engaging rib 42 will not engage actuator 32. This is for safety, to ensure that counter 80 is only advanced when an item is being disposed.

Figure 6A:
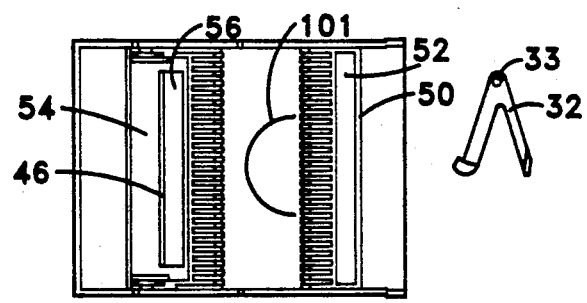

FIGS. 6A–6F show top-down view of rakes 40 and 44 and combs 50 and 54. Force 64 and shuttle 60 have been removed for clarity. In FIG. 6A, sharp 101 rests on partial floor 24 and the shuttle assembly is at its first position. Front comb tines 55 and front rake tines 45 are in alignment and parallel to protruding rail 46. Protruding rail 46 will not permit front comb 54 to be moved any further toward rear 14, as relative to front rake 44. Rear comb tines 51 and rear rake tines 41 are in alignment and parallel to protruding rail 46. Although removed, single force rail 63 will not permit rear comb 50 to be moved any further toward front 12, as relative to rear rake 40. As previously described, front rake 44 and rear rake 40 are on partial floor 24, front comb 54 is on front rake 44, and rear comb 50 is on rear rake 40.

Figure 6B:
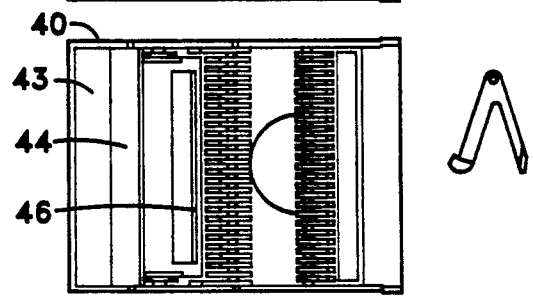

In FIG. 6B, the shuttle assembly is being moved from the first toward the second position. The spaced relationship of protruding rail 46 (and two parallel rails 63, not shown) and front comb rail receptacle 56 cause front rake tines 45 and front comb tines 55 to non-align, the front rake tines 45 being closer to rear 14 than front comb tines 55. The spaced relationship of single parallel rail 63, not shown, and rear comb force rail receptacle 52 cause rear comb tines 51 and rear rake tines 41 to non-align, the rear comb tines 51 being closer to rear 14 than rear rake tines 41. As shown, rear rake 40 is just ready to move toward rear 14, as will be caused by sharp 101.

Figure 6C:
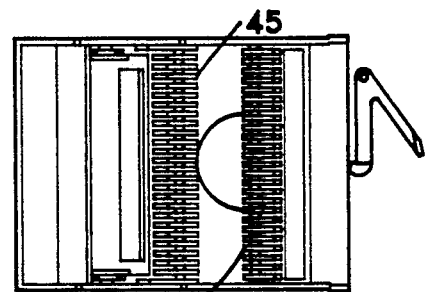

As shown in FIG. 6C, rakes 40 and 44 and combs 50 and 54 have maintained their spaced relationship as shown in FIG. 6B and moved toward rear 14, such that the shuttle assembly has reached its second position. Rib 42, not shown, has engaged the front tip of actuator 32, causing actuator 32 to rotate about mount 35 toward rear 14, thereby resulting in the rear tip of actuator 32 engaging counter activator means 81 to advance the reading on counter 80 to the next number. Sharp 101 to be disposed is now over drop window 22 in partial floor 24 of housing assembly 2 and should fall into drop area 94 of receptacle 90 for later disposal.

Figure 6D:
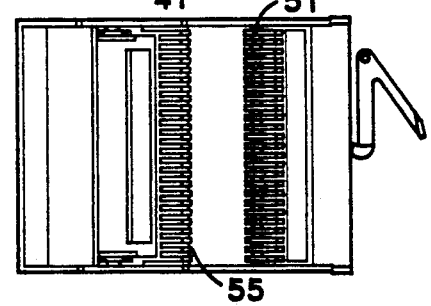
Figure 6E:
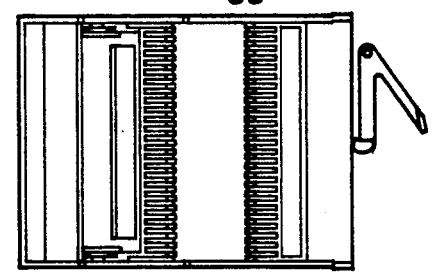

However, sharp items to be disposed, such as item 101, or very small items can become "caught" in rake tines 41 and 45. Therefore, with reference to FIGS. 6D and 6E, the combing action is shown which is designed to ensure items don't get caught in the rake tines 41 and 45. In FIG. 6D, the movement of the shuttle assembly from the second position to the first position has been initiated. Protruding rail 46 (and two parallel rails 63, not shown) in front comb rail receptacle 56 cause front rake tines 45 and front comb tines 55 to re-align and thereby comb-out any item caught in front rake tines 45. In FIG. 6E, front rake 44 and front comb 54 move in unison and single parallel rail 63, not shown, in rear comb force rail receptacle 52 cause rear comb tines 51 and rear rake tines 41 to re-align and thereby comb-out any item caught in rear rake tines 41.

Figure 6F:
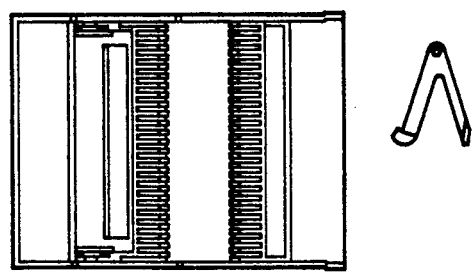

FIG. 6F matches FIG. 6A. The shuttle assembly has been returned to its first position. Actuator spring 34 has caused actuator 32 to rotate about mount 35 so that actuator 32 is no longer engaging counter activator means 81.

The foregoing detailed description is given primarily for clearness of understanding and no unnecessary limitations are to be understood therefrom for modifications can be made by those skilled in the art upon reading this disclosure and may be made without departing from the spirit of the invention and scope of the appended claims.

What is claimed is:

1. An apparatus for counting and disposing of expendable medical items, including sharps and the like, comprising:
   a. a housing assembly, said housing assembly including a counter and a removable receptacle for depositing items for disposal, said housing assembly having a partial floor therein; said housing assembly having a front and a rear; said counter having engagement means to advance counter to the next number; and,
   b. a movable shuttle assembly slidably received in and retained by said housing assembly, said shuttle assembly having a receiving opening therein, such that any item received into said receiving opening will be received on said partial floor of said housing assembly, whereby, when said shuttle assembly is slidably moved from a first position to a second position, any item on said partial floor is deposited in said removable receptacle and said counter advancer means is engaged to advance said counter to the next number.

2. The apparatus of claim 1, wherein said housing assembly further comprises: means to reset said counter when said removable receptacle is included into said housing assembly.

3. The apparatus of claim 2, wherein said counter reset means comprises: a reset tab on said counter and a counter resetter on said removable receptacle, whereby, when said removable receptacle is included into said housing assembly, said counter resetter on said removable receptacle engages said reset tab on said counter, thereby causing said counter to initialize to a zero reading.

4. The apparatus of claim 1, further comprising: means to position said movable shuttle assembly at said first position and necessitate that when said shuttle assembly is slidably moved, said movable shuttle assembly must be moved to said second position before said movable shuttle assembly can be returned to said first position.

5. The apparatus of claim 4, wherein said shuttle position means comprises:
   a. a support having a slot therein, said support attached to said shuttle assembly;
   b. a rectangular-shaped spring, said spring being inserted into said slot in said support and extending therefrom; and,
   c. a "C"-shaped recess in said partial floor of said housing assembly, said C-shaped recess having a C-side and an opening width that is wider at a front position and a rear position and narrower at positions between said front and said rear positions, said C-shaped recess receiving said rectangular-shaped spring; whereby, when said movable shuttle assembly is at said first position, said rectangular-shaped spring is in a relaxed condition in said front position of said C-shaped recess; when said movable shuttle assembly is slidably moved toward said second position, said rectangular-shaped spring bends toward said front position by engaging said C-side, thereby preventing said movable shuttle assembly from being returned to said first position until said movable shuttle assembly is at said second position, where said rectangular-shaped spring is in a relaxed condition in said rear position of said C-shaped recess.

6. The apparatus of claim 1, further comprising: means to only engage said counter advancer means when said shuttle assembly is moved from said first position to said second position and an item has been deposited into said receiving opening and received on said partial floor of said housing assembly.

7. The apparatus of claim 6, wherein said activation means comprises:
   a. a force having an opening therethrough, said opening in alignment with said receiving opening in said shuttle assembly; said force attached to said shuttle assembly and forming a part thereof; said force having a bottom surface, said bottom surface having a pair of downwardly-extending, rectangular-shaped, front force rails, said front force rails being in a parallel alignment;
   b. a rectangular-shaped rear rake having an opening therethrough, said opening in alignment with said receiving opening in said shuttle assembly; said rear rake having a pair of parallel side rails, a front rail connecting said parallel side rails toward said front of said housing assembly, and a counter actuating assembly connecting said parallel side rails toward said rear of said housing assembly; said counter actuating assembly having a plurality of rear rake tines opening toward said front of said housing assembly, a surface behind said plurality of rear rake tines toward said rear of said housing assembly, said surface having a downwardly-extending actuator-engaging rib, said rib being in a parallel relationship with said parallel side rails;
   c. a rectangular-shaped front rake, said front rake having a plurality of front rake tines opening toward said rear of said housing assembly; a surface before said plurality of front rake tines toward said front of said housing assembly, said surface having an upwardly-extending, rectangular-shaped, protruding rail, said surface further having a downwardly-extending support;

d. a "V"-shaped actuator having a front tip, a rear tip, and a base end, said actuator having a downwardly-extending bore therethrough at said base end;

e. an actuator spring;

f. a retainer having an opening therethrough;

g. a front rake support recess in said partial floor of said housing assembly;

h. an actuator recess in said partial floor of said housing assembly, said actuator recess having an upwardly-extending actuator mount therein, said actuator being contained in said actuator recess with said actuator mount extending upward into said base end actuator bore;

i. an actuator spring recess holding said actuator spring in a rest position so that said rear tip of said actuator does not engage said counter advancer means when said shuttle is at said first position; and, j. an actuator-engaging rib recess in said partial floor of said housing assembly;

said rear rake being on said partial floor of said housing assembly so said actuator-engaging rib can slide in said actuator-engaging rib recess to engage said front tip of said actuator; said front rake being on said partial floor of said housing assembly in said opening of said rear rake, said downwardly-extending front rake support being slidably contained in said front rake support recess; said front rake upwardly-extending protruding rail being inserted between said downwardly-extending front force rails; said force extending upwardly through said opening in said retainer; said retainer being fixedly attached to said housing assembly to slidably retain said force and thereby said movable shuttle assembly; whereby, when an item to be disposed is deposited into said receiving opening and received on said partial floor of said housing assembly and when said shuttle assembly is slidably moved from said first position to said second position, said item prevents said front rake tines from intermeshing with said rear rake tines, thereby causing said actuator-engaging rib to move toward said rear of said housing assembly engaging said front tip of said actuator thereby causing said rear tip of said actuator to move against said actuator spring toward said rear of said housing assembly and engage said counter advancer means to advance said counter to the next number, said item being deposited into said removable receptacle; but, if no item is present and said shuttle assembly is slidably moved from said first position to said second position, said front rake tines and said rear rake tines intermesh and said actuator-engaging rib does not cause said rear tip of said actuator to engage said counter advancer means.

8. The apparatus of claim 7, further comprising: means to comb items from said front rake tines and said rear rake tines.

9. The apparatus of claim 8, wherein said comb means comprises:

a. a single downwardly-extending, rectangular-shaped, rear force rail, said rear force rail attached to said bottom surface of said force at a location toward said rear of said housing assembly as related to said front force rails, said rear force rail being in a parallel alignment with said front force rails;

b. a rectangular-shaped front comb having a front comb rail receptacle therethrough, said front comb rail receptacle receiving said upwardly-extending protruding rail of said front rake and said pair of downwardly-extending front force rails, said front comb being on said surface of said front rake, said front comb having a plurality of front comb tines opening toward said rear of said housing assembly and intermeshing with and slidable between said plurality of front rake tines, as allowed by said protruding rail and said front force rails received in said front comb rail receptacle;

c. a rectangular-shaped rear comb having a rear comb rail receptacle therethrough, said rear comb receptacle receiving said downwardly-extending rear force rail, said rear comb being on said surface of said rear rake, said rear comb having a plurality of rear comb tines opening toward said front of said housing assembly and intermeshing with and slidable between said plurality of rear rake tines as allowed by said downwardly-extending rear force rail received in said rear comb rail receptacle;

whereby, when said shuttle assembly is at said first position said front rake tines and said front comb tines are in alignment relative to said front force rails and said rear rake tines and said rear comb tines are in alignment relative to said rear force rail; as said shuttle assembly is slidably moved from said first position toward said second position, said rear force rail in said rear comb rail receptacle causes said rear comb to initially slide toward said rear of said housing assembly before said rear rake, thereby non-aligning said rear rake tines and said rear comb tines, and said protruding rail and said pair of front force rails in said front comb rail receptacle cause said front rake to initially slide toward said rear of said housing assembly before said front comb, thereby non-aligning said front rake tines and said front comb tines; and these non-aligned tine positions are maintained until said shuttle assembly reaches said second position; and, as said shuttle assembly is slidably returned from said second position toward said first position, said rear force rail in said rear comb rail receptacle causes said rear comb to initially slide toward said front of said housing assembly before said rear rake, thereby realigning said rear rake tines and said rear comb tines and combing any item from said rear rake tines, and said protruding rail and said pair of front force rails in said front comb receptacle allow said front rake to initially slide toward said front of said housing assembly before said front comb, thereby realigning said front rake tines and said front comb tines and combing any item from said front rake tines.

10. The apparatus of claim 9, wherein said front comb further comprises: at least two comb spring notches and a comb spring for each said notch, wherein said comb spring is inserted into said notch thereby exerting a pressure onto said parallel side rails of said rear rake.

11. The apparatus of claim 1, wherein said second position is at least 1⅞" closer to said rear of said housing assembly than is said first position.

12. The apparatus of claim 1, further comprising: means to properly align said items for disposal received on said partial floor of said housing assembly.

13. The apparatus of claim 12, wherein said alignment means comprises: a magnet, said magnet being contained within a recess in said partial floor of said housing assembly and said magnet being located in said partial floor in alignment with said receiving opening in said shuttle assembly when said shuttle assembly is at said first position.

14. The apparatus of claim 1, said shuttle assembly further comprising: means to close said receiving opening in said shuttle assembly.

15. The apparatus of claim 14, wherein said closure means comprises: a safety slide, said safety slide being received by a safety slide opening in said shuttle assembly; said safety slide having a window protector toward said front of said housing assembly and an opening therebehind; said safety slide having an open position wherein said opening is aligned with said shuttle assembly receiving opening and said housing assembly partial floor therebelow, such that items can be received by said shuttle assembly receiving opening and received on said housing assembly partial floor therebelow; and said safety slide having a closed position wherein said window protector is between said shuttle assembly receiving opening and said housing assembly partial floor therebelow, thereby protecting a user when sliding said shuttle assembly from said first to said second position.

16. The apparatus of claim 1, wherein said shuttle assembly further comprises: means to cut.

17. The apparatus of claim 14, wherein said shuttle assembly further comprises: means to cut.

18. The apparatus of claim 15, wherein said shuttle assembly further comprises:
   a. a plate having an opening therethrough, said opening being in alignment with said shuttle assembly receiving opening and said housing assembly partial floor therebelow, said opening having a front side and a rear side, said plate having a raised blade receptacle located toward said rear of said housing assembly in relation to said opening in said plate;
   b a cutting blade, said cutting blade being mounted in said blade receptacle of said plate, said blade being in a parallel alignment with said plate, said blade extending into said opening in said plate from said rear toward said front side;
   c. a curved, rectangular-shaped, mandrell, said mandrell being inserted into a mandrell slot in said safety slide wherein said mandrell is at a location between said window protector and said opening therebehind of said safety slide, said mandrell being perpendicular to said cutting blade; whereby, when said safety slide is slidably moved from said open position to said closed position, said mandrell engages said cutting blade to shear from any item received into said shuttle assembly receiving opening any portion of said item extending thereabove.

19. The apparatus of claim 1, wherein said shuttle assembly further comprises: a window for viewing said counter.

20. An apparatus for counting and disposing of expendable medical items, including sharps and the like, comprising:
   a. a housing assembly, said housing assembly including a counter and a removable receptacle for depositing items for disposal, said housing assembly having a partial floor therein; said housing assembly having a front and a rear; said counter having engagement means to advance counter to the next number;
   b. a movable shuttle assembly slidably received in and retained by said housing assembly, said shuttle assembly having a receiving opening therein, such that any item received into said receiving opening will be received on said partial floor of said housing assembly, whereby, when said shuttle assembly is slidably moved from a first position to a second position, any item on said partial floor is deposited in said removable receptacle and said counter advancer means is engaged to advance said counter to the next number; said shuttle assembly having a window for viewing said counter;
   c. means to reset said counter when said removable receptacle is included into said housing assembly;
   d. means to position said movable shuttle assembly at said first position and necessitate that when said shuttle assembly is slidably moved, said movable shuttle assembly must be moved to said second position before said movable shuttle assembly can be returned to said first position;
   e. means to only engage said counter advancer means when said shuttle assembly is moved from said first position to said second position and an item has been deposited into said receiving opening and received on said partial floor of said housing assembly;
   f. means to ensure any item to be disposed is deposited in said removable receptacle when said shuttle assembly is at said second position; and,
   g. means to properly align said items for disposal received on said partial floor of said housing assembly.

21. The apparatus of claim 20, further comprising: means to close said receiving opening in said shuttle assembly and means to cut.

22. An apparatus for counting and disposing of expendable medical items, including sharps and the like, comprising:
   a. a housing assembly, said housing assembly including a counter and a removable receptacle for depositing items for disposal, said housing assembly having a partial floor therein; said housing assembly having a front and a rear; said counter having engagement means to advance counter to the next number; said shuttle assembly having a window for viewing said counter;
   b. a movable shuttle assembly slidably received in and retained by said housing assembly, said shuttle assembly having a receiving opening therein, such that any item received into said receiving opening will be received on said partial floor of said housing assembly, whereby, when said shuttle assembly is slidably moved from a first position to a second position, any item on said partial floor is deposited in said removable receptacle and said counter advancer means is engaged to advance said counter to the next number;
   c. a reset tab on said counter and a counter resetter on said removable receptacle, whereby, when said removable receptacle is included into said housing assembly, said counter resetter on said removable receptacle engages said reset tab on said counter, thereby causing said counter to initialize to a zero reading;
   d. a force having an opening therethrough, said opening in alignment with said receiving opening in said shuttle assembly; said force attached to said shuttle assembly and forming a part thereof; said force having a bottom surface, said bottom surface having a pair of downwardly-extending, rectangular-shaped, front force rails, said front force rails being in a parallel alignment;
   e. a rectangular-shaped rear rake having an opening therethrough, said opening in alignment with said receiving opening in said shuttle assembly; said rear rake having a pair of parallel side rails, a front rail connecting said parallel side rails toward said front of said housing assembly, and a counter actuating assembly connecting said parallel side rails toward said rear of said housing assembly; said counter actuating assembly having a plurality of rear rake tines opening toward said front of said housing assembly, a surface behind said plurality of rear rake tines toward said rear of said housing assembly, said surface having a downwardly-extending actuator-engaging rib, said rib being in a parallel relationship with said parallel side rails;

f. a rectangular-shaped front rake, said front rake having a plurality of front rake tines opening toward said rear of said housing assembly; a surface before said plurality of front rake tines toward said front of said housing assembly, said surface having an upwardly-extending, rectangular-shaped, protruding rail, said surface further having a downwardly-extending support; said support having a slot therein;

g. a rectangular-shaped spring, said spring being inserted into said slot in said support and extending therefrom;

h. a "C"-shaped recess in said partial floor of said housing assembly, said C-shaped recess having a C-side and an opening width that is wider at a front position and a rear position and narrower at positions between said front and said rear positions, said C-shaped recess receiving said rectangular-shaped spring; whereby, when said movable shuttle assembly is at said first position, said rectangular-shaped spring is in a relaxed condition in said front position of said C-shaped recess; when said movable shuttle assembly is slidably moved toward said second position, said rectangular-shaped spring bends toward said front position by engaging said C-side, thereby preventing said movable shuttle assembly from being returned to said first position until said movable shuttle assembly is at said second position, where said rectangular-shaped spring is in a relaxed condition in said rear position of said C-shaped recess;

i. a "V"-shaped actuator having a front tip, a rear tip, and a base end, said actuator having a downwardly-extending bore therethrough at said base end;

j. an actuator spring;

k. a retainer having an opening therethrough;

l. an actuator recess in said partial floor of said housing assembly, said actuator recess having an upwardly-extending actuator mount therein, said actuator being contained in said actuator recess with said actuator mount extending upward into said base end actuator bore;

m. an actuator spring recess holding said actuator spring in a rest position so that said rear tip of said actuator does not engage said counter advancer means when said shuttle is at said first position;

n. an actuator-engaging rib recess in said partial floor of said housing assembly; said rear rake being on said partial floor of said housing assembly so said actuator-engaging rib can slide in said actuator-engaging rib recess to engage said front tip of said actuator; said front rake being on said partial floor of said housing assembly in said opening of said rear rake, said downwardly-extending front rake support being slidably contained said front rake support recess; said front rake upwardly-extending protruding rail being inserted between said downwardly-extending front force rails; said force extending upwardly through said opening in said retainer; said retainer being fixedly attached to said housing assembly to slidably retain said force and thereby said movable shuttle assembly; whereby, when an item to be disposed is deposited into said receiving opening and received on said partial floor of said housing assembly and when said shuttle assembly is slidably moved from said first position to said second position, said item prevents said front rake tines from intermeshing with said rear rake tines, thereby causing said actuator-engaging rib to move toward said rear of said housing assembly engaging said front tip of said actuator thereby causing said rear tip of said actuator to move against said actuator spring toward said rear of said housing assembly and engage said counter advancer means to advance said counter to the next number, said item being deposited into said removable receptacle; but, if no item is present and said shuttle assembly is slidably moved from said first position to said second position, said front rake tines and said rear rake tines intermesh and said actuator-engaging rib does not cause said rear tip of said actuator to engage said counter advancer means;

o. a single downwardly-extending, rectangular-shaped, rear force rail, said rear force rail attached to said bottom surface of said force at a location toward said rear of said housing assembly as related to said front force rails, said rear force rail being in a parallel alignment with said front force rails;

p. a rectangular-shaped front comb having rail receptacle therethrough, said front comb rail receptacle receiving said upwardly-extending protruding rail of said front rake and said pair of downwardly-extending front force rails, said front comb being on said surface of said front rake, said front comb having a plurality of front comb tines opening toward said rear of said housing assembly and intermeshing with and slidable between said plurality of front rake tines, as allowed by said protruding rail and said front force rails received in said front comb rail receptacle;

q. a rectangular-shaped rear comb having a rear comb rail receptacle therethrough, said rear comb receptacle receiving said downwardly-extending rear force rail, said rear comb being on said surface of said rear rake, said rear comb having a plurality of rear comb tines opening toward said front of said housing assembly and intermeshing with and slidable between said plurality of rear rake tines as allowed by said downwardly-extending rear force rail received in said rear comb rail receptacle; whereby, when said shuttle assembly is at said first position said front rake tines and said front comb tines are in alignment relative to said front force rails and said rear rake tines and said rear comb tines are in alignment relative to said rear force rail; as said shuttle assembly is slidably moved from said first position toward said second position, said rear force rail in said rear comb rail receptacle causes said rear comb to initially slide toward said rear of said housing assembly before said rear rake, thereby non-aligning said rear rake tines and said rear comb tines, and said protruding rail and said pair of front force rails in said front comb rail receptacle cause said front rake to initially slide toward said rear of said housing assembly before said front comb, thereby non-aligning said front rake tines and said front comb tines; and these non-aligned tine positions are maintained until said shuttle assembly reaches said second position; and, as said shuttle assembly is slidably returned from said second position toward said first position, said rear force rail in said rear comb rail receptacle causes said rear comb to initially slide toward said front of said housing assembly before said rear rake, thereby realigning said rear rake tines and said rear comb tines and combing any item from said rear rake tines, and said protruding rail and said pair of front force rails in said front comb receptacle allow said front rake to initially slide toward said front of said housing assembly before said front comb, thereby realigning said front rake tines and said front comb tines and combing any item from said front rake tines;

r. said front comb including at least two comb spring notches and a comb spring for each said notch, wherein said comb spring is inserted into said notch thereby exerting a pressure onto said parallel side rails of said rear rake; and, s. a magnet, said magnet being contained within a recess in said partial floor of said housing assembly and said magnet being located in said partial floor in alignment with said receiving opening in said shuttle assembly when said shuttle assembly is at said first position.

23. The apparatus of claim 22, said shuttle assembly further comprising:

a. a safety slide, said safety slide being received by a safety slide opening is said shuttle assembly; said safety slide having a window protector toward said front of said housing assembly and an opening therebehind; said safety slide having an open position wherein said opening is aligned with said shuttle assembly receiving opening and said housing assembly partial floor therebelow, such that items can be received by said shuttle assembly receiving opening and received on said housing assembly partial floor therebelow; and said safety slide having a closed position wherein said window protector is between said shuttle assembly receiving opening and said housing assembly partial floor therebelow, thereby protecting a user when sliding said shuttle assembly from said first to said second position;

b. a plate having an opening therethrough, said opening being in alignment with said shuttle assembly receiving opening and said housing assembly partial floor therebelow, said opening having a front side and a rear side, said plate having a raised blade receptacle located toward said rear of said housing assembly in relation to said opening in said plate;

c. a cutting blade, said cutting blade being mounted in said blade receptacle of said plate, said blade being in a parallel alignment with said plate, said blade extending into said opening in said plate from said rear toward said front side;

d. a curved, rectangular-shaped, mandrell, said mandrell being inserted into a mandrell slot in said safety slide wherein said mandrell is at a location between said window protector and said opening therebehind of said safety slide, said mandrell being perpendicular to said cutting blade; whereby, when said safety slide is slidably moved from said open position to said closed position, said mandrell engages said cutting blade to shear from any item received into said shuttle assembly receiving opening any portion of said item extending thereabove.

* * * * *